(12) United States Patent
Brenneman

(10) Patent No.: US 7,731,897 B2
(45) Date of Patent: *Jun. 8, 2010

(54) FORMATS FOR OPTICAL ANALYSIS AND METHODS OF MANUFACTURING THE SAME

(75) Inventor: Allen J. Brenneman, Goshen, IN (US)

(73) Assignee: Bayer HealthCare LLC, Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/252,133

(22) Filed: Oct. 15, 2008

(65) Prior Publication Data

US 2009/0040515 A1    Feb. 12, 2009

Related U.S. Application Data

(63) Continuation of application No. 10/576,992, filed as application No. PCT/US2004/036086 on Oct. 29, 2004, now Pat. No. 7,494,620.

(60) Provisional application No. 60/515,337, filed on Oct. 30, 2003.

(51) Int. Cl.
G01N 21/01    (2006.01)
B23P 11/00    (2006.01)

(52) U.S. Cl. ............... 422/58; 422/55; 422/50; 356/246; 356/244; 436/68; 436/136

(58) Field of Classification Search .............. 422/58, 422/55, 50; 436/165, 86; 356/246, 244; 29/464, 466, 428, 592
See application file for complete search history.

(56) References Cited

U.S. PATENT DOCUMENTS 4,756,884 A    7/1988    Hillman et al. ............ 422/73

| 5,035,494 A | 7/1991 | Foldenauer | 350/536 |
| 5,148,596 A | 9/1992 | Zahn | 29/842 |
| 5,337,468 A | 8/1994 | Zahn | 29/842 |
| 5,371,020 A | 12/1994 | Frischauf | 436/165 |
| 5,525,518 A | 6/1996 | Lundsgaard et al. | 436/68 |
| 5,564,419 A | 10/1996 | Lundsgaard et al. | 600/317 |

(Continued)

FOREIGN PATENT DOCUMENTS

EP    0418993 A2    3/1991

(Continued)

OTHER PUBLICATIONS

International Search Report for International Application No. PCT/US2004/036086, European Patent Office, filed Oct. 29, 2005 mailing date Jan. 28, 2005, 5 pages.

(Continued)

*Primary Examiner*—Walter D Griffin
*Assistant Examiner*—Christine T Mui
(74) *Attorney, Agent, or Firm*—Nixon Peabody LLP

(57) ABSTRACT

Formats for the optical testing of fluids are manufacturing using modular format components. The format components are constructed so that matching format components can be mated together to form a single format for optical testing. Formats may be manufactured using pin-and-hole construction so that pins on optical format components mate with holes on opposing format components. Optical read surfaces provided on optical format components oppose each other in a completed optical format to form a read area.

19 Claims, 5 Drawing Sheets

U.S. PATENT DOCUMENTS

| | | | |
|---|---|---|---|
| 5,616,053 A | 4/1997 | Bogursky et al. | 439/590 |
| 5,620,086 A | 4/1997 | Bianca et al. | 200/542 |
| 5,706,952 A | 1/1998 | Bianca et al. | 206/713 |
| 5,725,392 A | 3/1998 | Bianca et al. | 439/590 |
| 5,749,458 A | 5/1998 | Bianca et al. | 200/541 |
| 5,938,996 A | 8/1999 | Bianca et al. | 264/145 |
| 5,957,725 A | 9/1999 | Bianca et al. | 439/590 |
| 5,957,739 A | 9/1999 | Bianca et al. | 439/885 |
| 5,967,841 A | 10/1999 | Bianca et al. | 439/590 |
| 6,123,820 A | 9/2000 | Bergkuist et al. | |
| 6,202,853 B1 | 3/2001 | Bianca et al. | 206/713 |
| 6,391,541 B1 * | 5/2002 | Petersen et al. | 435/5 |
| 2002/0079218 A1 * | 6/2002 | Brenneman et al. | 204/400 |

FOREIGN PATENT DOCUMENTS

| | | | |
|---|---|---|---|
| EP | 0418993 | B1 | 1/1996 |
| EP | 0753901 | A2 | 1/1997 |
| EP | 0785709 | A2 | 7/1997 |
| EP | 0843389 | A2 | 5/1998 |
| EP | 0847112 | A1 | 6/1998 |
| EP | 0872920 | A2 | 10/1998 |
| EP | 0753901 | B1 | 10/2000 |
| EP | 0847112 | B1 | 3/2001 |
| EP | 0785709 | B1 | 5/2001 |
| EP | 0695937 | B1 | 5/2002 |
| EP | 1215479 | A2 | 6/2002 |
| FR | 2 835 617 | | 2/2002 |

OTHER PUBLICATIONS

Written Opinion of the International Searching Authority for International Application No. PCT/US2004/036086, European Patent Office, filed Oct. 29, 2005 mailing date Jan. 28, 2005, 6 pages.

* cited by examiner

FORMATS FOR OPTICAL ANALYSIS AND METHODS OF MANUFACTURING THE SAME

CROSS-REFERENCE TO RELATED APPLICATIONS

This application is a continuation of U.S. patent application Ser. No. 10/576,992, filed on Apr. 25, 2006, which is a U.S. national stage of International Application No. PCT/US2004/036086, filed on Oct. 29, 2004, which claims the benefit of priority to U.S. Provisional Application No. 60/515,337, filed on Oct. 30, 2003, each of which is hereby incorporated by reference herein in its entirety.

FIELD OF THE INVENTION

The present invention relates generally to medical testing and more specifically to optical analysis of fluids using an optical format.

BACKGROUND OF THE INVENTION

In recent years, various types of medical analysis have become increasingly decentralized and more accessible to the patient. The testing of bodily fluids represents one example of this decentralization. Many tests that previously had to be performed at a doctor's office and perhaps even analyzed at a separate office can now be performed immediately and inexpensively in the comfort of a patient's home. One example of such a test is blood glucose monitoring, which is widely used among diabetic patients.

Optical analysis has presented itself as one convenient method for analyzing bodily fluids. In a typical optical analysis application, a certain amount of fluid is placed in a read area adapted to allow light to pass through the fluid or to reflect or diffuse upon contact with the fluid. The light as altered by the fluid can then be collected and analyzed, with changes in the light indicating medically significant properties of the fluid. Fluid may be directed to a read area using a "format," or a platform for collecting and handling the fluid.

A problem arises in that the fluid volumes used for such analyses is very small—typically in the range of from about 50 nl to about 250 nl, though not limited to any given volume. It is preferable to enable testing with a small sample volume, but such a small sample volume calls for the use of a small read area or window upon which the sample is placed and through which light is passed for analysis. Further, the small sample size requires tight tolerances in the manufacture of formats for optical testing. To ensure consistent analysis from sample to sample, it is important to minimize format-to-format variations in the path light travels through an optical format. Any variability in optical path length directly impacts the magnitude of a transmission signal. Smaller sample sizes drive the need for increased consistency in format construction. Solutions to address the problem of optical path length variation between manufactured formats have resulted in costly precision cuvettes, complex molding techniques, or long optical path lengths to minimize the impact of path length tolerance. None of these solutions is ideal for high-production-volume, low cost, and low-sample-volume systems.

One type of format uses a base member with a cover member adhesively connected to the base member. In these formats, the placement of adhesive between the cover and the base is one source of variation in optical path length that tends to reduce the sample-to-sample precision of testing.

There is a need for optical formats that are efficient to manufacture and easy to use, and that result in precise measurements.

SUMMARY OF THE INVENTION

According to some embodiments of the present invention, an optical format for sample analysis is manufactured of identical format components that snap together.

According to some embodiments of the present invention, optical format components having alignment pins and alignment holes are mated to each other to form optical formats having very little light path variation from format to format.

According to some embodiments of the present invention, an optical format is manufactured in a continuous molding process.

According to some embodiments of the present invention, a continuous molding process may make use of reels to result in molded optical format components attached to reels.

According to some embodiments of the present invention, optical format components having reagent chemicals applied thereto are mated with identical optical format components without reagent chemicals to result in a fully constructed optical format with reagent chemicals in a sample analysis area.

Figure 1:
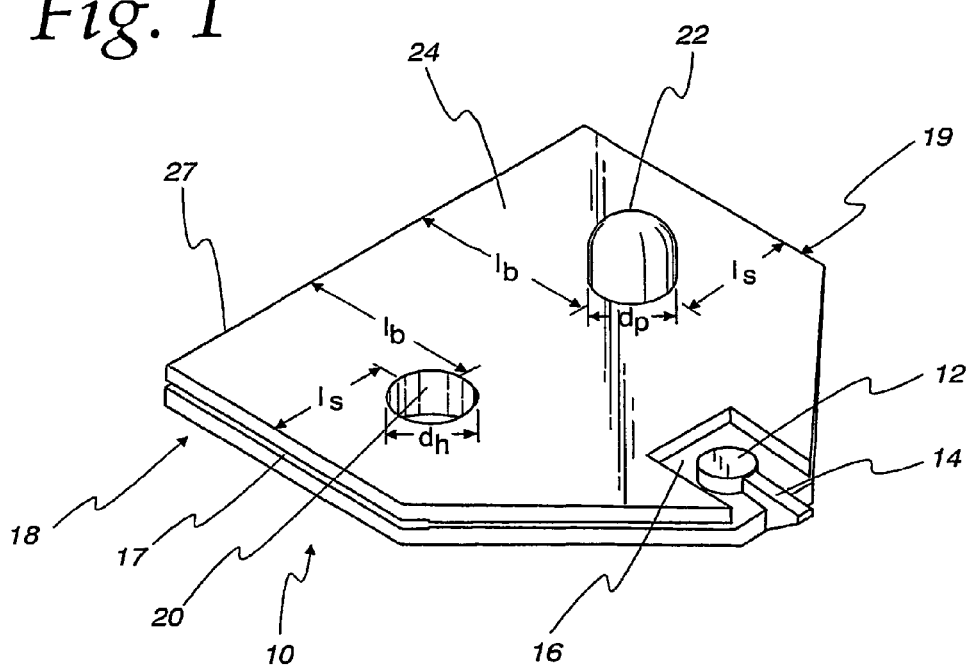
FIG. 1 is a perspective view of an optical format component according to one embodiment of the present invention.

While the invention is susceptible to various modifications and alternative forms, specific embodiments are shown by way of example in the drawings and will be described in detail herein. However, it should be understood that the invention is not intended to be limited to the particular forms disclosed. Rather, the invention is to cover all modifications, equivalents, and alternatives falling within the spirit and scope of the invention as defined by the appended claims.

DESCRIPTION OF SPECIFIC EMBODIMENTS

In optical testing of fluids for medical purposes, such as the transmission or reflection spectrophotometry of blood or interstitial fluid for glucose concentration measurements, instruments and techniques which reduce the complexity of the required medical devices or provide for easier interaction with the user are of great value. Turning to FIG. 1, an optical format component 10 according to one embodiment of the present invention is shown. The optical format component 10 is capable of forming a reliable optical format, significantly increasing the production efficiency for optical testing instruments, and further increasing ease of testing. The optical format component 10 of FIG. 1 is designed to be joined with another optical format component to form an optical format. The optical format component 10 includes a read surface 12 upon which a sample is deposited for analysis. An inlet surface 14 extends outwardly from the read surface 12 and serves to direct sample fluid from outside an optical format toward the read surface 12. The read surface 12 and the inlet surface 14 may be formed within a format cavity 16. Slots 17 along the sides 18 and 19 of the optical format component 10 may ease handling and transportation of the optical format component 10.

A hole 20 in the optical format component 10 is positioned to enable construction of an optical format when another optical format component is attached to the optical format component 10. A pin 22 projects from the inner surface 24 of the optical format component 10. According to one embodiment of the present invention, the optical format component 10 forms an optical format when it is joined with an identical or substantially identical optical format component, which is inverted atop the optical format component 10. According to the embodiment shown in FIG. 1, the centers of the hole 20 and the pin 22 are positioned a distance $l_b$ from a rear surface 27 of the format component and a distance $l_s$ from the side surfaces 25 and 29 of the format component. The pin 22 has a diameter $d_p$ and the hole 20 has a diameter $d_h$. According to some embodiments, the diameter $d_h$ of the hole 20 and the diameter $d_p$ of the pin are approximately equal to assure a tight fit between pins and their corresponding holes when optical formats are constructed. Pins according to some embodiments of the present invention may be provided with vertical crush ribs to provide a tighter interference fit. The number of hole/pin combinations and their placement on format components 10 may be changed according to the desired size of the format components and the location of critical features of the format. It is preferred to provide enough hole/pin combinations to hold the format together for all post-assembly operations, such as packaging, shipping, and testing. The pin and hole features are not limited to cylindrical forms, but can be of many different cross-sectional shapes. An exploded view of an optical format formed when two format components are joined together is shown in FIG. 2.

Figure 2:
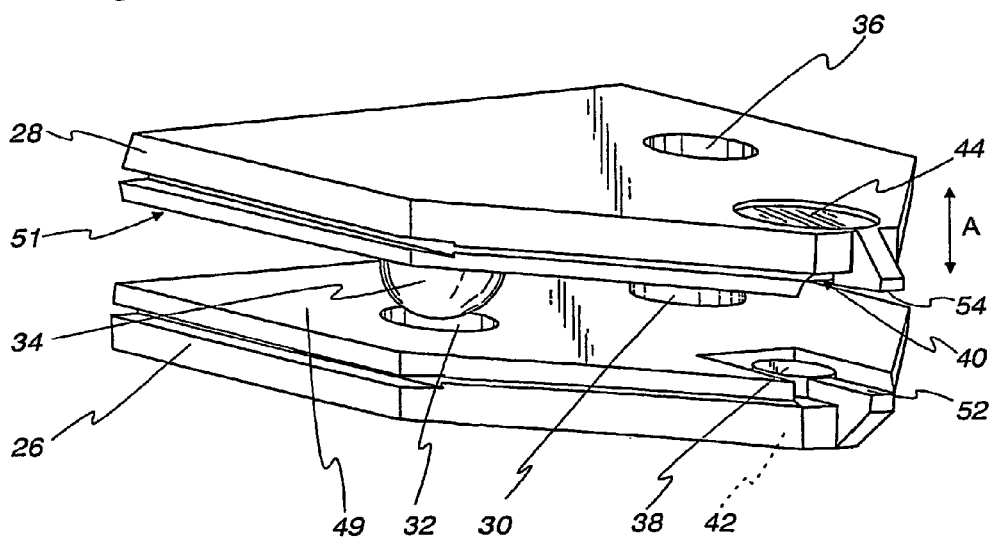
FIG. 2 is an isometric exploded view of an optical format according to one embodiment of the present invention.

Turning now to FIG. 2, a first optical format component 26 is shown in the process of being joined to a second optical format component 28 to form an optical format according to one embodiment of the present invention. The first optical format component 26 is provided with a first pin 30 and a first hole 32; likewise the second optical format 28 is provided with a second pin 34 and a second hole 36. To facilitate construction of an optical format from the first and second optical format components 26 and 28, it is preferred to provide the pins with rounded tips, as shown on the second pin 34.

Figure 3:
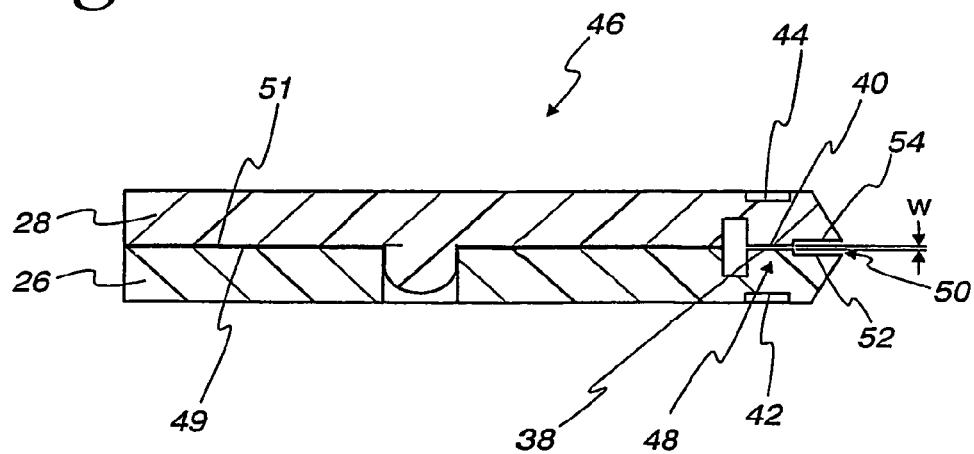
FIG. 3 is a cross-sectional side view of an optical format according to one embodiment of the present invention.

To form an optical format according to one embodiment of the present invention, the first and second optical format components 26 and 28 are moved together in the direction shown by arrow "A" of FIG. 2. Thus, the first pin 30 is inserted into the second hole 36 and the second pin 34 is inserted into the first hole 32. A first read surface 38 and a second read surface 40 are separated from each other when the optical format is constructed to form a read area, where a sample is held during testing. According to one embodiment of the present invention, the first optical format component 26 and the second optical format component 28 are made of optically clear or substantially optically clear material. In this embodiment, a first optical window 42 (whose position is shown by the dotted line) provided on the lower surface of the first optical format component 26 of FIG. 2, and a second optical window 44 allow light to pass through the read area for optical testing of a sample within the read area 48 (shown in FIG. 3). As shown in FIG. 2, the area of a first inner surface 49 of the first optical format component 26 is large in comparison to the area of the first read surface 38. Likewise, the area of a second inner surface 51 of the second optical format component 28 is large in comparison to the area of the second read surface 40. The width w of the read area 48 is governed by the height difference between the first inner surface 49 and the first read surface 38 and further by the height difference between the second inner surface 51 and the second read surface 40. When the first and second inner surfaces 49 and 51 abut each other, as shown in FIG. 3, a stable formation results in an interface between the two surfaces, reducing variations in the width w of the read area 48 from one optical format to another when many optical formats are produced. According to some embodiments of the present invention, the interface between the first and second inner surfaces is free of connecting materials or connecting areas such as adhesives, sonic welding ribs, or other features that could potentially change the dimensions and tolerances of the capillary gap and optical read path of the format.

Turning now to FIG. 3, a cross-sectional side view of an assembled optical format 46 according to one embodiment of the present invention is shown. The read area 48 may comprise a capillary gap holding the sample within the read area. A fill capillary gap 50 may be formed by a first inlet surface 52 and a second inlet surface 54.

According to one embodiment of the present invention, the first optical format component 26 and the second optical format component 28 are identical or substantially identical. The first and second optical format components may be held together by friction between the pins 30 and 34 and the holes 36 and 32. Additional or alternative connection techniques may be used to hold the pins and holes together. According to some embodiments, the pins 30 and 34 are sonically welded into the holes 36 and 32. Additionally or alternatively, the pins 30 and 34 and the holes 36 and 32 may be joined by adhesive at the pin-hole mating interface. It is preferred to assure that adhesive does not attach to the inner surfaces of the optical format components, as adhesive on these inner surfaces adversely affects the uniformity of optical path length in the construction of optical formats.

Figure 4:
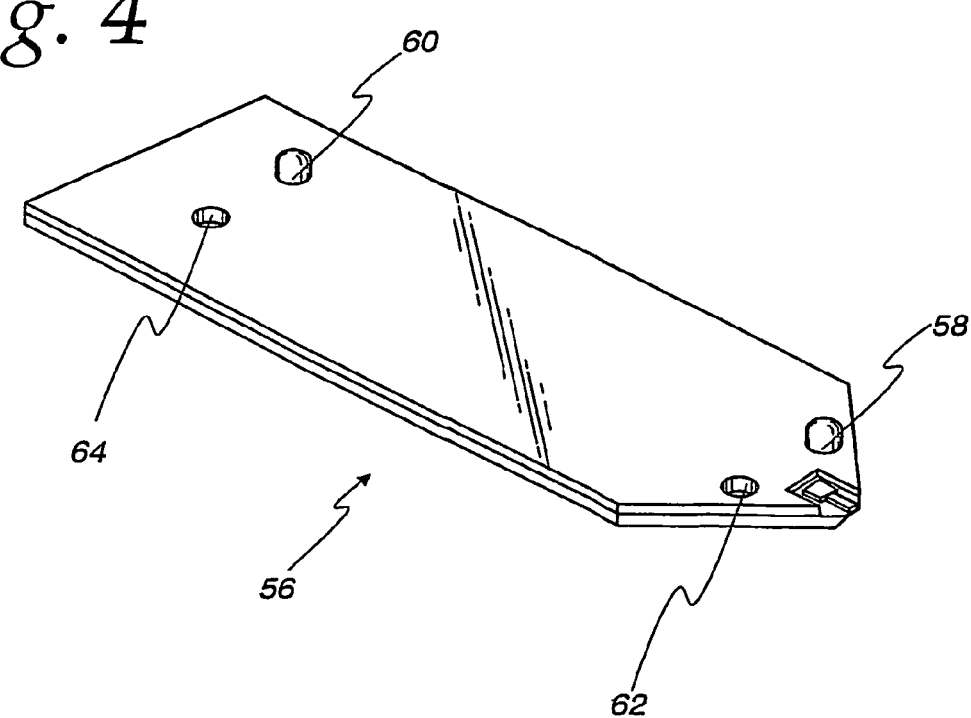
FIG. 4 is an isometric view of an optical format component according to one embodiment of the present invention.

It is to be understood that more than two pin-and-hole connections could be used to construct optical formats according to the present invention, as may be beneficial in certain applications of the present invention. For example, FIG. 4 shows an optical format component 56 according to one embodiment of the present invention featuring first and second pins 58 and 60 and first and second holes 62 and 64. A multiple-pin optical format component may be useful when a longer optical format component is desirable. For example, the longer optical format 56 of FIG. 4 is easier for a user to handle than a shorter optical component.

Figure 5A:
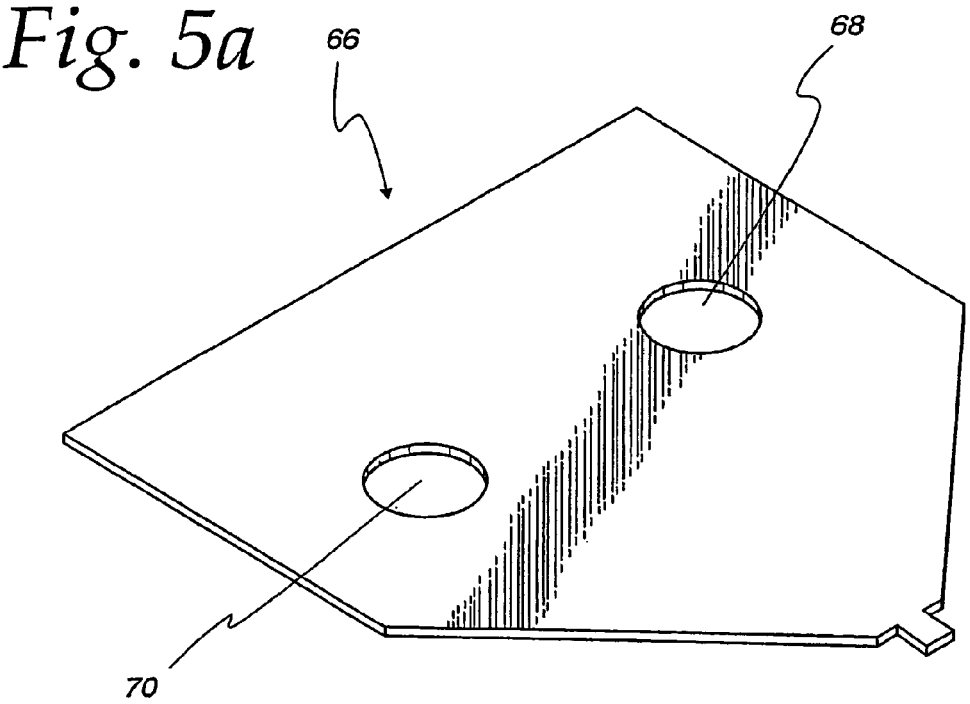
FIGS. 5a and 5b are isometric views of optical format components according to one embodiment of the present invention.
Figure 5B:
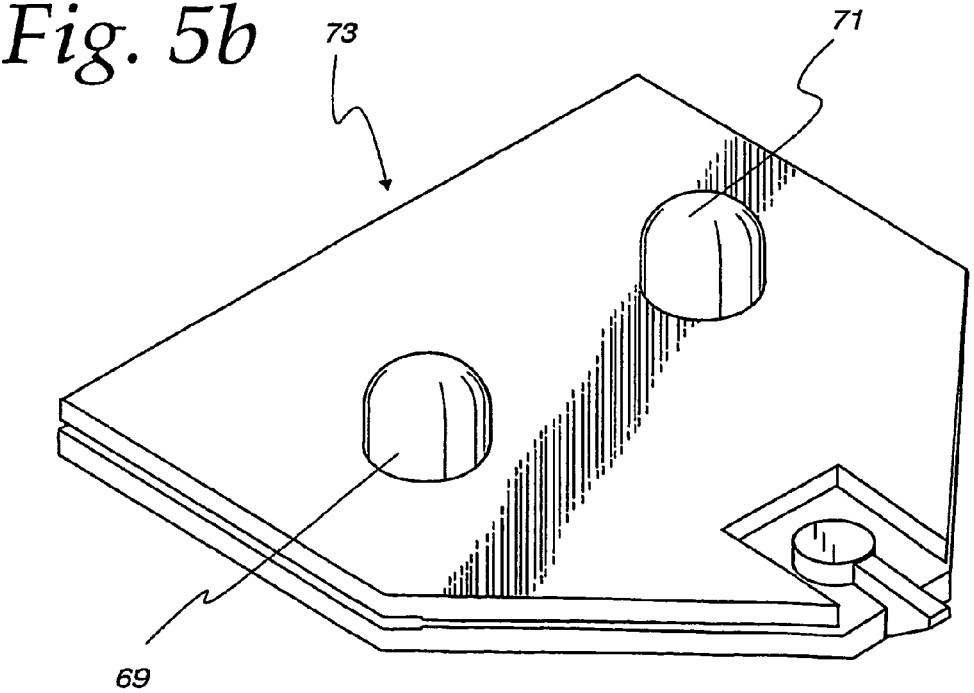

Optical formats according to some embodiments of the present invention may be manufactured using different types of optical format components. For example, rather than joining identical or substantially identical optical format components as shown in FIG. 2, an optical format may be formed by a base component having pins and no holes, and a lid member having holes and no pins. FIG. 5a shows one embodiment of a lid component 66 having first and second holes 68 and 70 adapted to mate with first and second pins 69 and 71 on a base component 73, as shown in FIG. 5b. Lid and base components such as the lid component 66 and base component 73 may be formed by molding or by punching from clear plastic stock.

Optical format components and optical formats according to the present invention may be manufactured using a number of manufacturing techniques and may be constructed of a variety of materials. Optical format components may be molded, embossed, coined, or manufactured using a combination of these processes, and may be constructed of materials such as acrylic, polycarbonate, and polyester.

Figure 6:
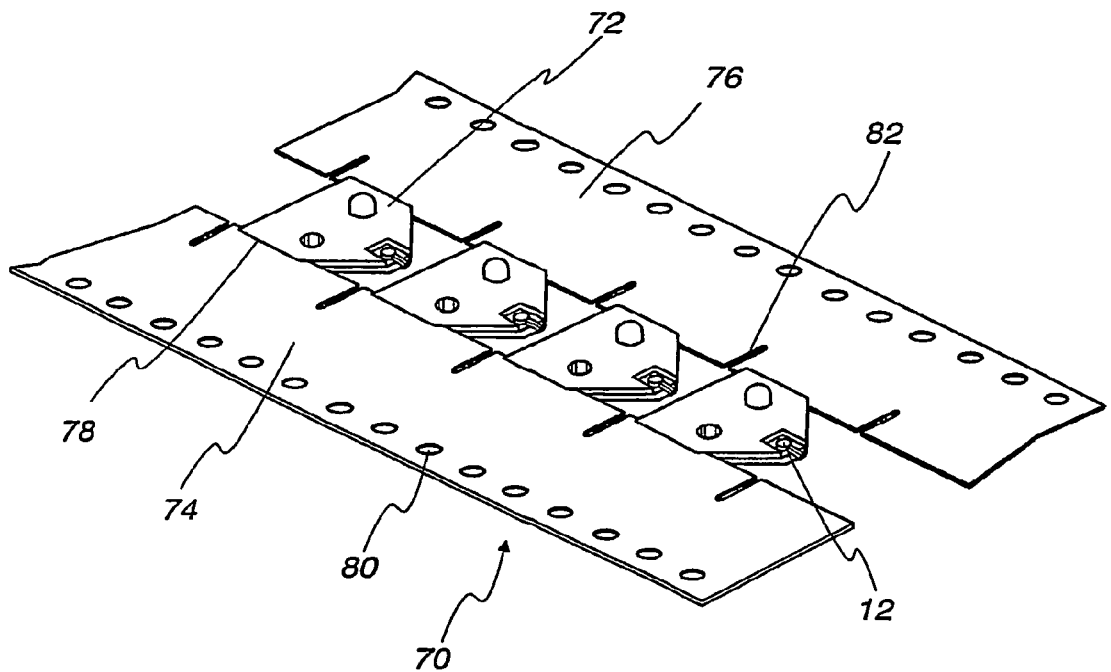
FIG. 6 is an isometric view of optical format components following formation according to one embodiment of the present invention.

Turning now to FIG. 6, a strip 70 of optical format components 72 is shown. The strip 70 has been formed by a continuous molding process employing first and second ribbons 74 and 76. Each of the optical format components 72 has been molded on the first and second ribbons 74 and 76 and these ribbons hold the optical format components in place. Slots 78 provided on the optical format components 72 are the result of removing the format in a post-molding operation. The slots have value for alignment of the format during processes such as packaging and inserting the format into a final diagnostic meter. Molding of the optical format components 72 may be accomplished by multi-cavity injection-molding, by which several optical format components 72 are molded at once. Optical format components 72 made by this process are held in one orientation until the components are removed from the ribbons 74 and 76. According to one embodiment of the molding process, the ribbons 74 and 76 are made of Mylar™ and are provided with guide holes 80 for advancement along a production machine and slits 82 to allow easy removal of molded optical format components 72.

Following molding of the optical format components 72, chemical reagents as required in particular embodiments of optical formats according to the present invention may be applied to read surfaces 12 of the optical format components. Following deposition of the reagent, the reagent may be dried. Optical format components with reagent applied to read surfaces may next be mated with optical format components with or without reagent applied to their read surfaces, as shown in FIG. 7.

Figure 7:
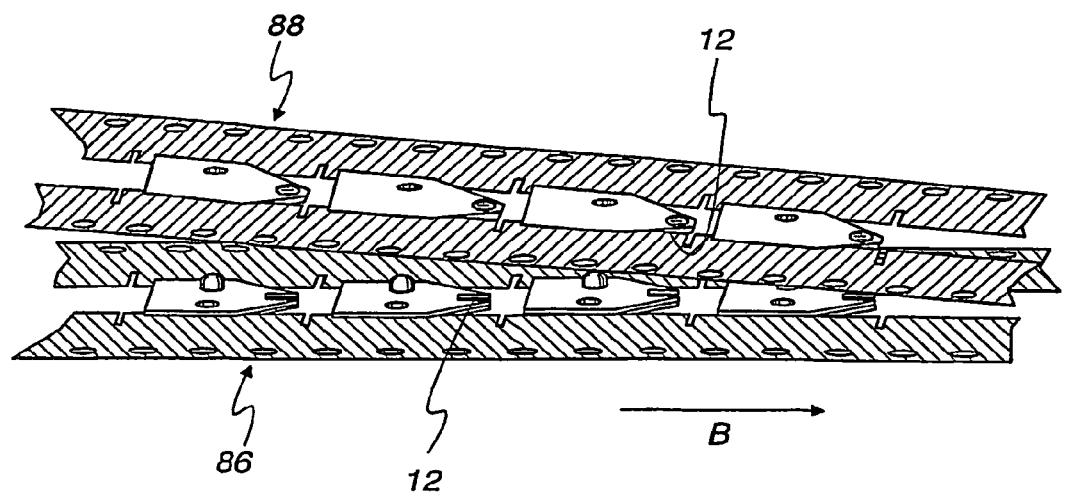
FIG. 7 is an isometric view of optical format components being joined together according to one embodiment of the present invention.

FIG. 7 shows a first strip 86 of optical format components being joined to a second strip 88 of optical format components. Either the first strip 86, the second strip 88, neither strip, or both strips of optical format components may be provided with reagent on their read surfaces 12. In the embodiment shown in FIG. 7, the first and second strips 86 and 88 of optical format components have substantially identical shapes, such that as the strips are moved in the direction shown by arrow "B," and approach each other, the optical format components will join together to result in optical formats. The optical format components may be sonically welded or connected via adhesives at the pin-hole interfaces at this point. Joined optical formats may be left on the strips to dispense as needed, or may be picked off the strips and placed into containers or wrapped individually.

Figure 8:
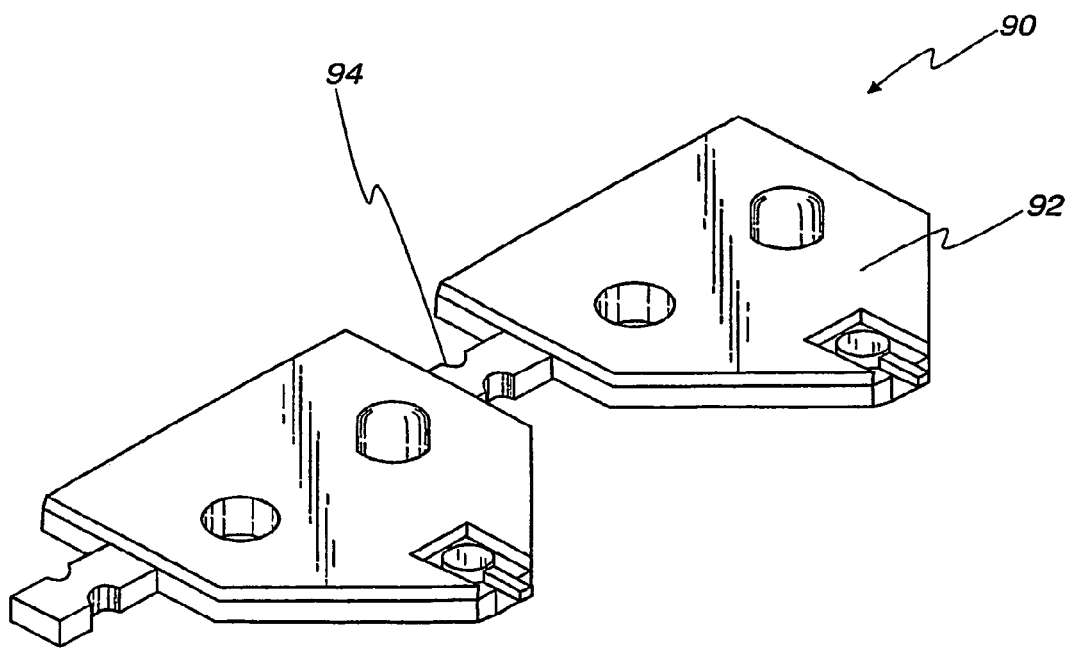
FIG. 8 is an isometric view of optical format components following formation according to one embodiment of the present invention.

Alternative manufacturing processes may be used to manufacture optical format components according to some embodiments of the present invention. For example, FIG. 8 shows a two-component chain 90 of optical format components 92. In this embodiment of the present invention, the optical format components 92 are joined to each other by links 94. Chains 90 of optical format components may be molded, reeled, and joined together similarly to the process described above with respect to FIG. 7, including the deposition of reagent chemicals on the optical format components. Similarly to the process shown in FIG. 7, optical formats formed as chains may be packaged in strips of several optical formats, wrapped and sold individually, or separated after formation and sold in containers holding multiple optical formats.

According to one embodiment of the present invention, optical format components are formed of optically clear or substantially optically clear materials. When two optical format components, such as the first and second optical format components 26 and 28 of FIGS. 2 and 3, are molded of optically clear or substantially optically clear materials, light may pass directly through an optical format through optical windows and through the sample. Alternatively, a first optical format component may be clear and a second optical format component may be opaque. Such a construction may be used in measurements based on light reflectance or diffusion rather than light transmission.

Optical formats according to the present invention may be packaged and sold as individual optical formats or packaged and sold as multiple formats on format strips.

While the present invention has been described with reference to one or more particular embodiments, those skilled in the art will recognize that many changes may be made thereto without departing from the spirit and scope of the present invention. For example, while the present invention has been generally described as directed to medical applications it is to be understood that any optical fluid testing applications might employ the principles of the invention. Each of these embodiments and obvious variations thereof is contemplated as falling within the spirit and scope of the claimed invention, which is set forth in the following claims.

What is claimed is:

1. A format for the optical analysis of a sample, said format comprising:
    a first format component having a first format component pin, a first inlet surface, and a first read surface; and
    a second format component forming a second format component hole, a second inlet surface, and a second read surface,
    wherein said first format component pin is inserted into said second format component hole such that said first read surface and said second read surface align to form a read area and said first inlet surface and said second inlet surface align to form a capillary gap that is open on a plurality of sides.

2. The format of claim 1, wherein said first read surface and said first inlet surface are disposed within a first format component cavity and said second read surface and said second inlet surface are disposed within a second format component cavity.

3. The format of claim 1, wherein said first and second format components are optically clear, said first format component comprises a first format component inner surface and a first format component outer surface and said second format component comprises a second format component inner surface and a second format component outer surface, said first format component having a first optical window disposed on said first format component outer surface and approximately aligned with said first read surface, and said second format component having a second optical window disposed on said second format component outer surface and approximately aligned with said second read surface, said first optical window, said read area, and said second optical window aligning to form an optical path.

4. The format of claim 1, wherein said second format component is approximately identical to said first format component.

5. The format of claim 1, wherein said first format component comprises a first format component inner surface and said second format component comprises a second format component inner surface, said first format component pin and said second format component hole meet at a pin-hole meeting interface, said pin-hole interfaces being joined with a sonic weld.

6. The format of claim 1, wherein said first format component is optically clear and comprises a read window aligned with said first read surface.

7. The format of claim 1, wherein said first format component comprises a first inner format surface, said second component comprises a second inner format surface, and said first and second format components are held together via friction between aligning pairs of said holes and pins forming an interface between said first inner format surface and said second inner format surface, such that said first inner format surface and said second inner format surface abut one another substantially completely, said interface between said first inner format surface and said second inner format surface being substantially free of adhesive or other intervening material.

8. The format of claim 1, wherein a reagent is applied to at least one of said first read surface and said second read surface.

9. A method of forming a format for the optical analysis of a sample, said method comprising:
   forming a first format component comprising a first format component pin, a first format component hole, a first inlet surface, and a first read surface;
   forming a second format component comprising a second format component pin, a second format component hole a second inlet surface, and a second read surface;
   aligning said first and second format components such that said first inlet surface is approximately aligned with said second inlet surface to form a capillary gap that is open on a plurality of sides and said first read surface is approximately aligned with said second read surface;
   inserting said first format component pin into said second format component hole; and
   inserting said second format component pin into said first format component hole.

10. The method of claim 9 further comprising sonically welding at least one of said first and second component pins to its corresponding format component hole.

11. The method of claim 9 further comprising applying a reagent to at least one of said first read surface and said second read surface.

12. The method of claim 9, wherein said first format component is optically clear and further comprises a read window approximately aligned with said first read surface.

13. The method of claim 9, wherein said first and second format components are optically clear and wherein said first format component comprises a first read window approximately aligned with said first read surface and said second format component comprises a second read window approximately aligned with said second read surface.

14. A format for the optical analysis of a sample, said format comprising:
   a first format component having at least one first format component pin, a first format component inner surface, a first inlet surface, and a first read surface; and
   a second format component having at least one second format component hole, a second format component inner surface, a second inlet surface, and a second read surface,
   wherein said first format component pin is inserted into said second format component hole, said first format component inner surface and said second format component inner surface abut at an inner surface interface, said second inlet surface and said first inlet surface align to form a fill capillary gap that is open on multiple sides, and said first read surface and said second read surface align to form a read area.

15. The format of claim 14, wherein said first format component inner surface and said second format component inner surface abut each other substantially completely and said inner surface interface is substantially free of adhesive or other intervening material.

16. The format of claim 14, wherein said first read surface and said first inlet surface are disposed within a first format component cavity and said second read surface and said second inlet surface are disposed within a second format component cavity.

17. The format of claim 14, wherein said first and second format components are optically clear, said first format component further comprises a first format component outer surface and said second format component further comprises a second format component outer surface, said first format component having a first optical window disposed on said first format component outer surface and approximately aligned with said first read surface, and said second format component having a second optical window disposed on said second format component outer surface and approximately aligned with said second read surface, said first optical window, said read area, and said second optical window aligning to form an optical path.

18. The format of claim 14, wherein said at least one first format component pin is sonically welded into said at lease one second format component hole.

19. The format of claim 14 further comprising a reagent applied to at least one of said first read surface and said second read surface.

* * * * *